United States Patent
Bryan

(10) Patent No.: US 9,533,109 B2
(45) Date of Patent: Jan. 3, 2017

(54) BUBBLE ENTRAPMENT DEVICE

(75) Inventor: Keith Bryan, Cork (IE)

(73) Assignee: CORK INSTITUTE OF TECHNOLOGY, Cork (IE)

(*) Notice: Subject to any disclaimer, the term of this patent is extended or adjusted under 35 U.S.C. 154(b) by 0 days.

(21) Appl. No.: 13/513,097

(22) PCT Filed: Dec. 20, 2010

(86) PCT No.: PCT/IE2010/000078
§ 371 (c)(1),
(2), (4) Date: Jul. 6, 2012

(87) PCT Pub. No.: WO2011/077420
PCT Pub. Date: Jun. 30, 2011

(65) Prior Publication Data
US 2012/0265139 A1  Oct. 18, 2012

(30) Foreign Application Priority Data
Dec. 22, 2009 (IE) .................................. 2009/0967

(51) Int. Cl.
*A61M 5/36* (2006.01)
*A61M 1/36* (2006.01)

(52) U.S. Cl.
CPC ............. *A61M 5/36* (2013.01); *A61M 1/3627* (2013.01)

(58) Field of Classification Search
CPC ............................. A61M 1/3267; A61M 5/365
USPC ........................................................... 604/122
See application file for complete search history.

(56) References Cited

U.S. PATENT DOCUMENTS

| | | | |
|---|---|---|---|
| 2,742,976 A * | 4/1956 | Toth et al. | 55/442 |
| 3,477,208 A * | 11/1969 | Keller, Sr. | 96/408 |
| 3,778,973 A | 12/1973 | Martinez | |
| 3,795,088 A * | 3/1974 | Esmond | 96/182 |
| 4,002,432 A * | 1/1977 | Brice et al. | 208/100 |
| 4,102,655 A | 7/1978 | Jeffery et al. | |
| 4,177,147 A | 12/1979 | Roberts | |
| 4,214,883 A * | 7/1980 | Raseley et al. | 96/189 |
| 4,433,971 A | 2/1984 | Lindsay et al. | |
| 5,503,801 A | 4/1996 | Brugger | |
| 7,097,690 B2 | 8/2006 | Usher et al. | |
| 7,279,031 B1 | 10/2007 | Wright | |
| 2010/0218679 A1 | 9/2010 | Hekmat et al. | |

OTHER PUBLICATIONS

International Search Report and Written Opinion for PCT/IE2010/000078 mailed May 13, 2011.

* cited by examiner

*Primary Examiner* — Aarti B Berdichevsky
(74) *Attorney, Agent, or Firm* — Hauptman Ham, LLP

(57) ABSTRACT

A bubble entrapment device includes at least one entrapment chamber between an inlet and an outlet. The chamber outlet port is approximately in the center, and so bubbles will rise in the chamber into a space above the chamber outlet port.

71 Claims, 18 Drawing Sheets

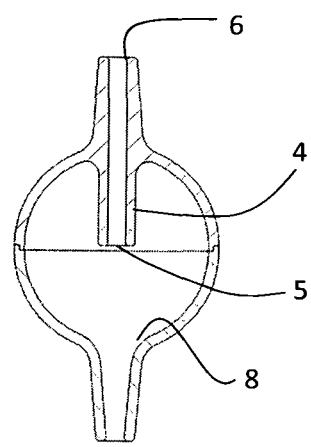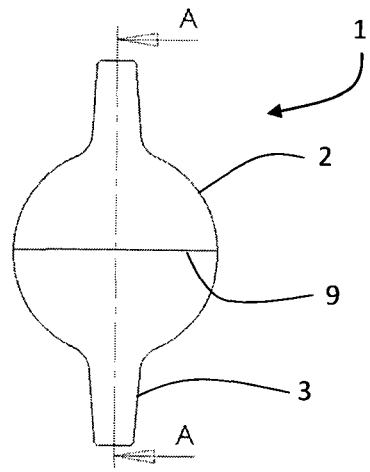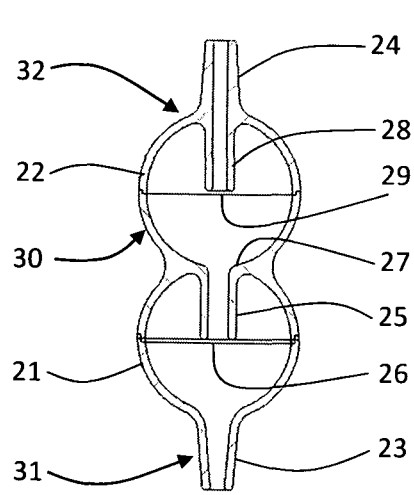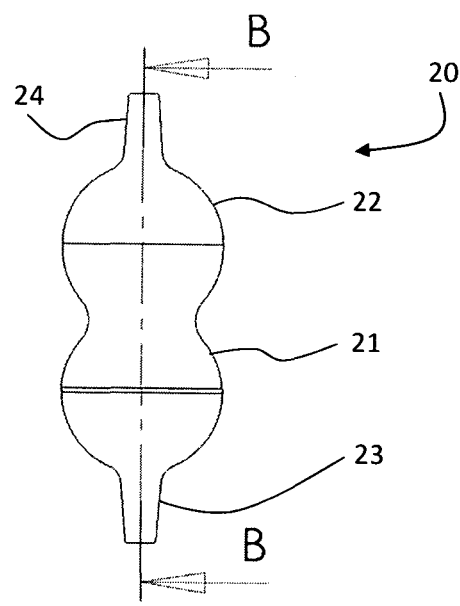

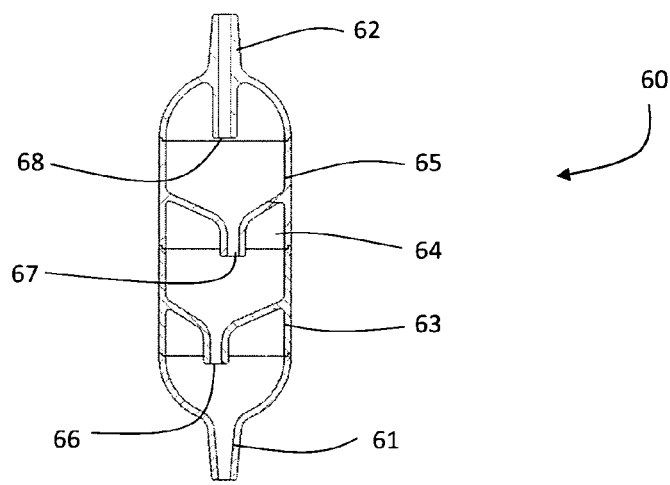
Fig.7
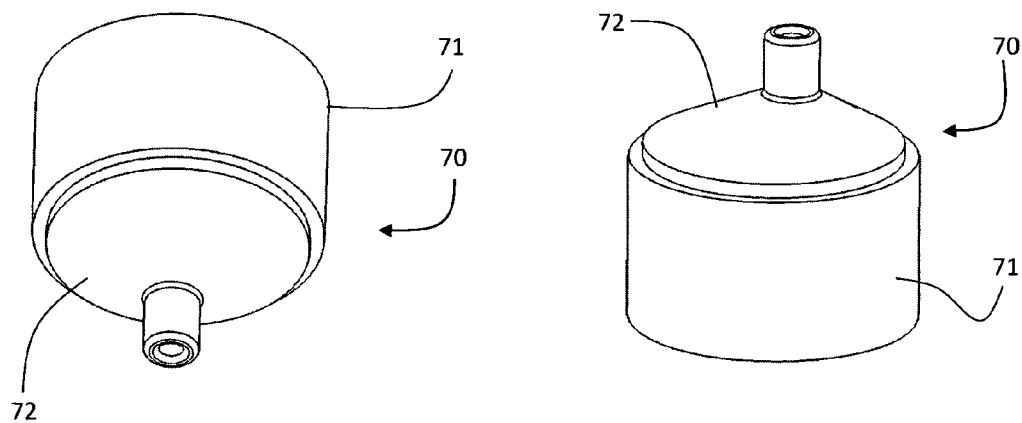
Fig.8
Fig.9

SECTION A-A

SECTION A-A

SECTION B-B

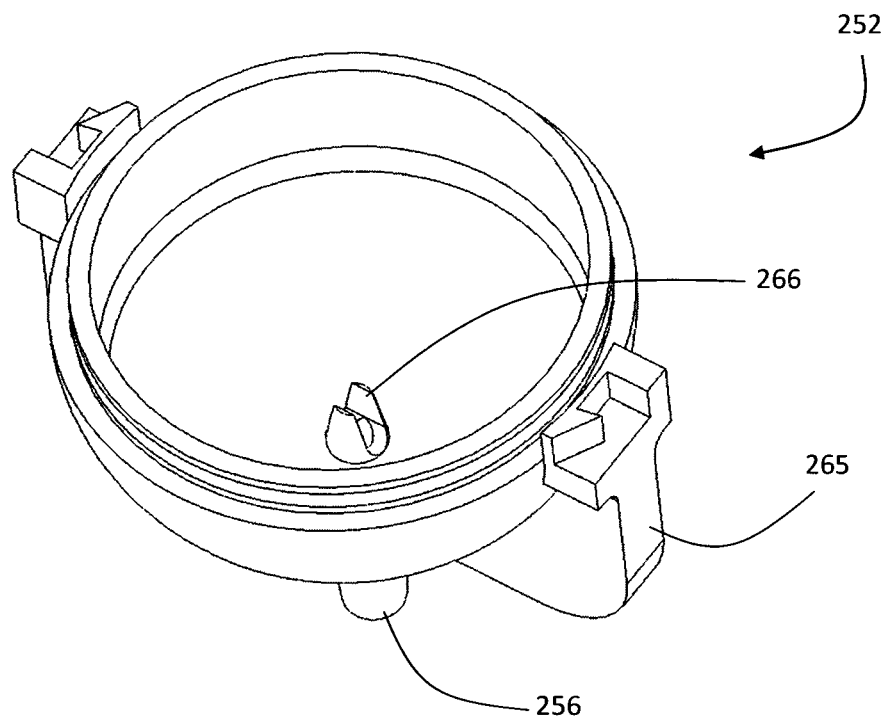
Fig.35
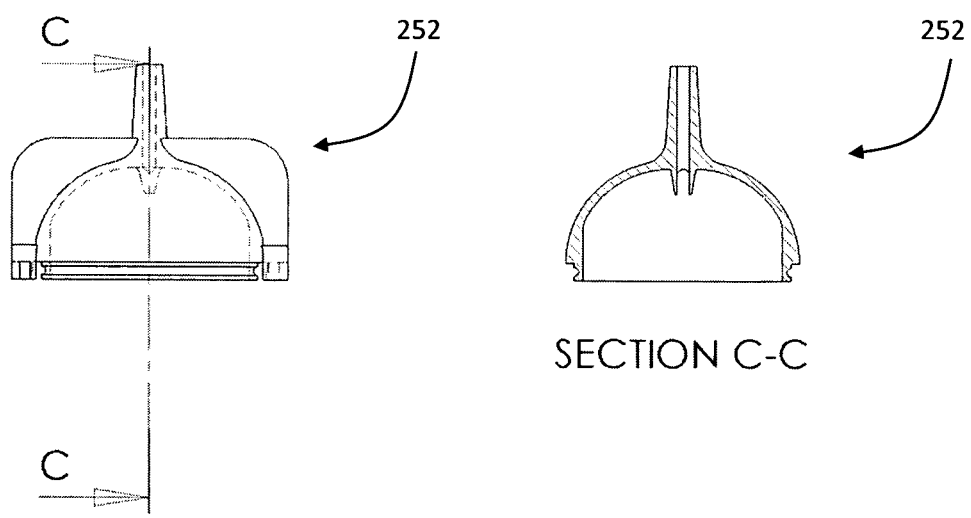
Fig.36
SECTION C-C
Fig.37

BUBBLE ENTRAPMENT DEVICE

RELATED APPLICATIONS

The present application is a national phase of PCT/IE2010/000078 and is based on, and claims priority from, Ireland Application Number 2009/0967, filed Dec. 22, 2009.

FIELD OF THE INVENTION

The invention relates to flow of fluid on a small scale, with flow rates greater than in typical microfluidic systems, but less than large-scale systems such as plumbing systems. An example is a medical device, such as an infusion system.

PRIOR ART DISCUSSION

There are a number of situations where it is desirable to ensure that bubbles do not flow in a conduit past a particular point. An example is an infusion system, for which it is very important that air bubbles do not pass into the patient. When administering any fluid intravenously, there is a risk of air or gas being transferred to the blood stream. An accumulation of this will cause an air embolism with the potential for severe morbidity and mortality. In practice it is common for nurses to tap the tube and bag to cause bubbles to rise to the surface in the bag. However, this is unsatisfactory as it is unreliable and time-consuming, and in some situations may put a patient at risk of a gas embolism.

U.S. Pat. No. 4,177,149 describes a filter assembly for intravenous liquid administration. This is an intrusive approach which is not desirable in many situations. Also, US20100218679 describes an air filtration system in which bubbles are removed in a trap having a chamber with an inner wall and an outer wall, the inner wall being permeable to gas but not liquid. U.S. Pat. No. 7,097,690 describes a trap in which layers of gas permeable membrane material are used to construct a filter structure.

The invention is directed towards providing a bubble entrapment device which is of simpler construction, and/or which has improved effectiveness. The invention is also directed towards providing improved medical devices for liquid flow to a patient's body.

SUMMARY OF THE INVENTION

According to the invention, there is provided a bubble entrapment device comprising a device inlet for receiving a flow of liquid, and a device outlet for outlet of liquid flow. There is a chamber between said device inlet and said device outlet. The chamber has an inlet port and an outlet port for liquid flow through the chamber. The chamber outlet port is located on a conduit and is within the chamber volume, providing in use a space for entrapment of bubbles within the chamber above the chamber outlet port.

In one embodiment, the outlet port is located approximately in the range of 30% to 70% across all dimensions across the chamber volume. Preferably, the range is 40% to 60%, and most preferably the outlet port is located approximately centrally in the chamber volume.

In one embodiment, there is a series of a plurality of chambers between the device inlet and the device outlet.

In one embodiment, the chamber outlet port is offset from a device central axis. In one embodiment, there are a plurality of chambers, and outlet ports of at least two chambers are offset from the device axis.

In another embodiment, the chamber conduit has a funnel-shaped configuration.

In one embodiment, there are a plurality of chambers and at least one chamber is linked by a tube with a next chamber.

In one embodiment, the chamber external walls are substantially spherical in configuration.

In one embodiment, at least one chamber is flexible to allow gas to be manually expelled by squeezing the chamber.

In one embodiment, the device comprises a plurality of interconnected modular units.

In one embodiment, the units comprise mid-section units and end cap units, and at least one mid-section unit comprises a central tube and a cup configured to form portion of a chamber at each end. In one embodiment, said cup portions have an approximate hemispherical or cylindrical configuration.

In one embodiment, the device is configured to be worn by a patient.

In one embodiment, the device comprises connectors at ends so that it can form a loop such as a bracelet.

In one embodiment, the device further comprises a valve to switch the device between a venting mode at which bubbles are allowed to flow through the device and a use mode for bubble entrapment.

In one embodiment, the valve is adapted to move a chamber outlet port from a location adjacent a chamber wall for the venting mode to a location within the chamber volume for the use mode.

In one embodiment, the valve comprises a plunger comprising at least one chamber outlet port and forming a chamber conduit, the plunger being adapted to move longitudinally with respect to the chamber to move the chamber outlet port. Preferably, the device comprises a plurality of chambers, and the plunger extends into a plurality of chambers and has an outlet port for each of said chambers. In one embodiment, the valve comprises a lock to prevent switching back to a venting mode after it has been in the use mode.

In one embodiment, the valve comprises a plunger comprising at least one chamber outlet port and forming a chamber conduit, the plunger being adapted to move longitudinally with respect to the chamber to move the chamber outlet port, and wherein the lock comprises a catch arranged to prevent sliding of the plunger from a use position to a venting position.

In one embodiment, the valve comprises a rotatable member with at least one chamber outlet port, in which the chamber outlet port moves upon rotation of the valve member.

In one embodiment, the valve has a handle for user gripping.

In one embodiment, the valve comprises a fixed conduit and an inner or outer rotatable sleeve, the conduit and the sleeve having outlet ports, the valve having the venting mode when the ports are in registry.

In one embodiment, the valve is integral with two chamber parts. In one embodiment, said two parts are mutually rotatable about a device axis, and each chamber part comprises an on-axis valve part, and said on-axis valve parts are configured to allow venting at one mutual position and to provide entrapment at another mutual position. In one embodiment, one valve part comprises a tube with at least one aperture at an end thereof, and the other valve part comprises a cover arranged to cover said aperture or apertures at one position for entrapment, and to leave them open at another position for venting.

In one embodiment, the chamber is of a transparent material.

In one embodiment, the chamber is of a flexible material.

In one embodiment, the device further comprises a filter to block unwanted particles.

In another aspect, the invention provides a medical system comprising a tube for delivering a liquid to the body, the system comprising a bubble entrapment device as defined above in any embodiment having its device inlet connected to a tube supply side and its device outlet connected to a tube delivery side.

In one embodiment, the entrapment device is adapted to be looped to be worn as a bracelet.

In one embodiment, the system is an infusion system.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 1 is a front view of a bubble entrapment device of the invention, and FIG. 2 is a cross-sectional view of this device;

FIGS. 3 and 4 are front and cross-sectional views of a device having two chambers;

FIG. 7 is a cross-sectional view of a three-chamber device,

FIGS. 8 and 9 are perspective views of a mid-section repeat unit of a device of a further embodiment;

FIG. 10 is a cross-sectional view of a further bubble entrapment device, having a plunger for switching from a venting mode to a use mode, in which FIG. 10 shows the venting mode and FIG. 11 shows the use mode;

FIGS. 30 to 39 are views of a further device, having one chamber, and in which a "half" is rotated for switching between venting and use modes, in which:

FIG. 30 is a cross-sectional view for venting,

FIG. 31 is a cross-sectional view for use,

FIG. 32 is a perspective view of an inlet half, FIG. 33 is a side view, and FIG. 34 is a cross-sectional view, FIG. 35 is a perspective view of an outlet half, FIG. 36 is a front view; and FIG. 37 is a cross-sectional view, and FIGS. 38 and 39 are cut-away perspective views of the full device in venting and use modes.

DESCRIPTION OF THE EMBODIMENTS

Figure 5:
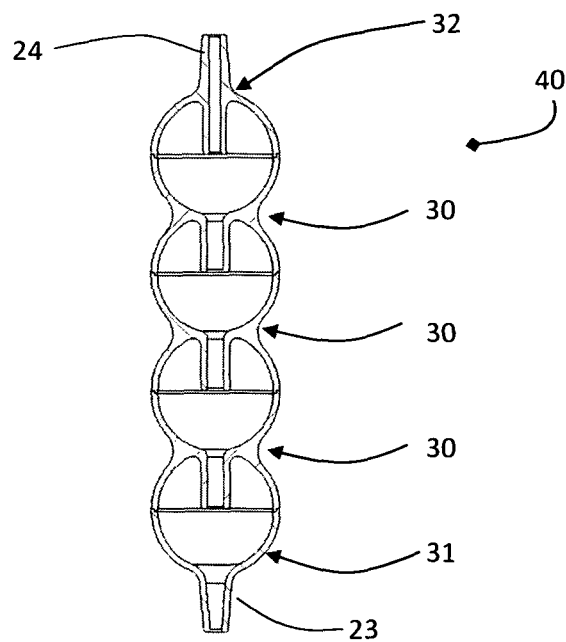
FIG. 5 is a cross-sectional view of a device having four chambers.

Bubble entrapment devices of the invention comprise a series of at least one entrapment chamber between a device inlet and a device outlet. Within each chamber, the chamber outlet port is on a conduit within the chamber and is approximately in the centre of the chamber's volume. The principle of operation is that a bubble will always float and if the exit from each chamber is near the centre of the chamber's volume the bubble will not pass unless the device is only about half full. Hence, due to gas buoyancy bubbles will rise in the chamber into a space which does not include the chamber outlet port provided the chamber is more than half full. This pertains irrespective of the chamber's orientation. The device is very effective with one chamber, but providing more than one chamber gives further reduced risk of a bubble passing through.

The chamber conduit may have a frusto-conical configuration, and the narrow end may be offset from a device central axis. The orientations (about the device axis) of conduits of successive chambers may be different, achieved by mutual rotation of units of the device about the axis upon manufacture or in-field assembly. The device will only work in one flow direction and is configured and/or marked at the inlet and outlet so that it can only be connected and used in the correct flow direction. The uni-directional aspect is convenient for some medical applications such as infusion systems, where it is desired to prevent bubbles from flowing in one direction but to allow them to flow easily in the other direction for initial purging.

As chamber outlets of successive chambers may be rotationally offset with respect to each other the device will operate even if it is oriented vertically.

For many applications it is desirable that bubbles be trapped in one direction only as the other direction is advantageously used for purging, allowing bubbles to advantageously flow through. However in other embodiments a device of the invention may have at least one chamber in reverse orientation for bi-directional bubble entrapment.

Referring to FIGS. 1 and 2 a bubble entrapment device 1 has a chamber 2, an inlet 3, a chamber conduit 4 with a chamber outlet port 5, and a device outlet port 6. The device 1 is of plastics material, preferably transparent polycarbonate (or alternatively polyurethane) joined around the circumference of the chamber 2 at edges 9.

Irrespective of the orientation of the device 1, any bubbles entering the device 1 with liquid will rise up to the highest point in the chamber volume and can not exit via the conduit 5 unless the device is approximately half full of air. The device 1 is therefore a very simple and effective way of ensuring that bubbles do not progress to the device outlet 6.

The chamber outlet port 5 is best located centrally in the chamber. The preferred range of location is 40% to 60% of a dimension across the chamber in any direction. While the chamber outlet port may be located at say 30% of the distance from a chamber wall in one dimension across the chamber, then it is possible that a gas bubble can pass through at a certain device orientation (with the port uppermost) when the chamber is up to 70% full. While this might be satisfactory in certain situations, it is not preferred when the orientation of the device can change during use. For most applications it is preferred that the chamber outlet port be located in the range of 40% to 60% across all chamber dimensions.

Figure 6:
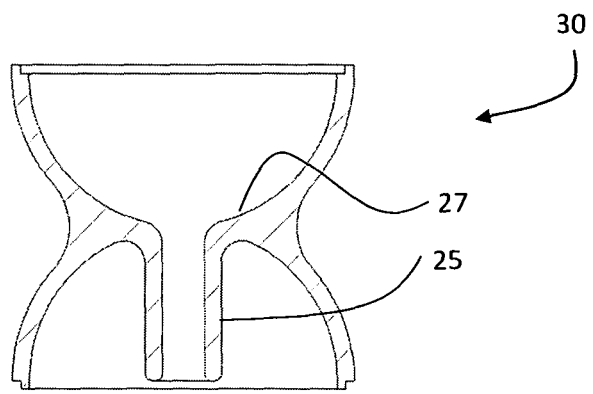
FIG. 6 shows a mid-section repeat unit of this device.

During operation the bubbles may be periodically purged by temporarily reversing the fluid flow. This procedure can also be used to remove air from the chamber(s) of the device with the fixed exit conduit(s) when priming prior to use Referring to FIGS. 3 and 4 a device 20 has an inlet 23, a series of two chambers 21 and 22 and an outlet 24. The first chamber 21 has a conduit 25 with a chamber outlet port 26 and the second chamber 22 has a chamber conduit 28 with a chamber outlet port 29. The device 20 is assembled from a mid-section unit 30, an inlet cap 31, and an outlet cap 32 joined together. This allows very efficient and versatile manufacturing, or even assembly in the field. FIGS. 5 and 6 demonstrate the versatility, showing a device 40 having four chambers formed by three mid-section units 30, the inlet cap 31, and the outlet cap 32. A mid-section unit 30 is shown more clearly in FIG. 6, showing a chamber inlet port 27 at the top end of the conduit 25.

FIG. 7 shows a device 60 having a device inlet 61, a device outlet 62, three chambers 63, 64, and 65 having chamber conduits 66, 67, and 68 respectively.

FIGS. 8 and 9 show mid-section repeat units 70 for an alternative device. Each unit 70 has a cylindrical chamber wall 70, and a conduit 72. The units 70 may be mutually rotated, ensuring that the successive conduits 72 are not aligned, further reducing risks of bubbles travelling along if the device is exactly vertical.

In other embodiments the entrapment device includes a valve to allow an initial venting mode in which bubbles do easily pass through, followed by a use mode in which they are trapped as described above. In these embodiments the chamber outlet port is effectively movable in the field between the top of the chamber volume and a position at or near its centre. The switching is preferably non-reversible.

Figure 10:
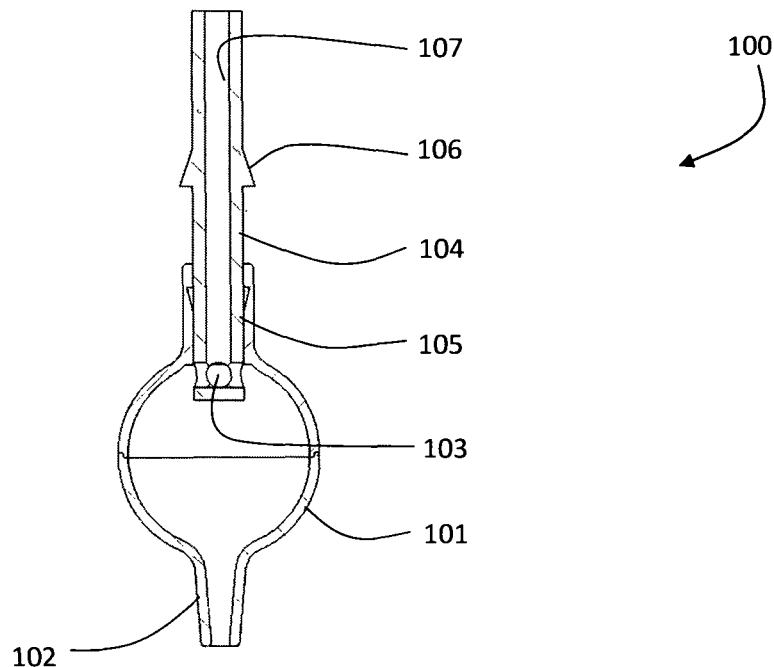
Figure 11:
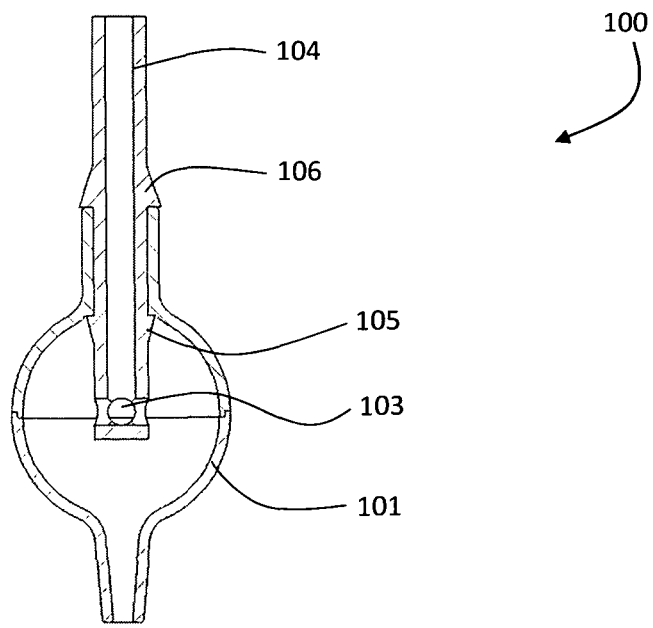

Referring to FIGS. 10 and 11 a device 100 has a chamber 101, a device inlet 102 and a chamber outlet port 103 on a valve plunger 104. The latter has a circumferential catch 105 and a circumferential stop ridge 106. In a venting mode (FIG. 10) bubbles freely move with the liquid from the top of the chamber 101 out through the port 103 and the central duct 107 in the plunger 104. However, when the plunger 104 is pushed down the catch 105 engages in the chamber to prevent it from being pulled back up, and the stop ridge 106 prevents excessive pushing. The chamber outlet port 103 is then located for bubble entrapment as shown in FIG. 11.

Figure 12:
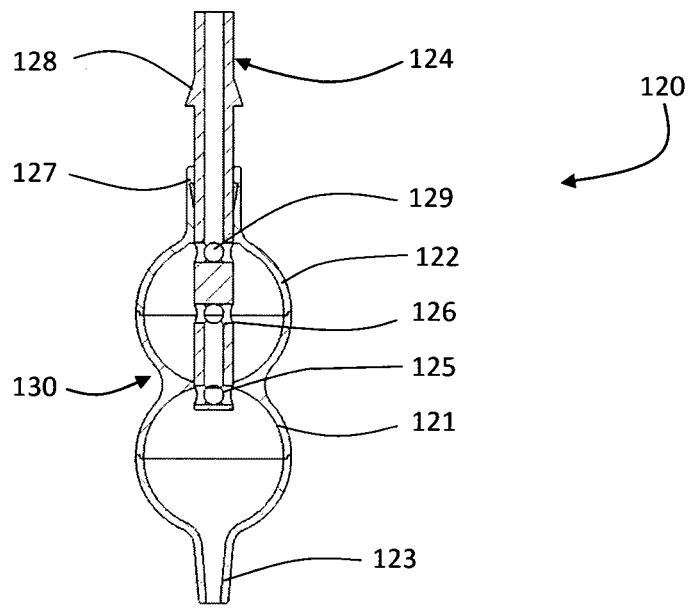
FIGS. 12 and 13 are cross-sectional views of a two-chamber version of the embodiment of FIGS. 10 and 11, and for this device
Figure 13:
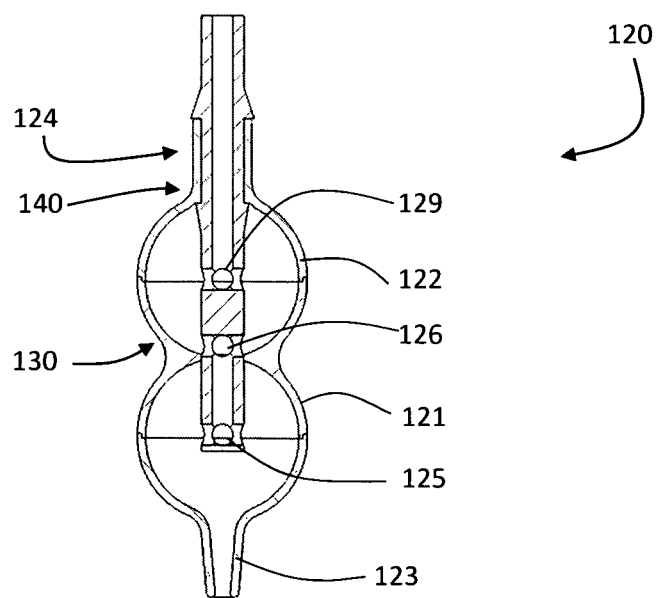
Figure 14:
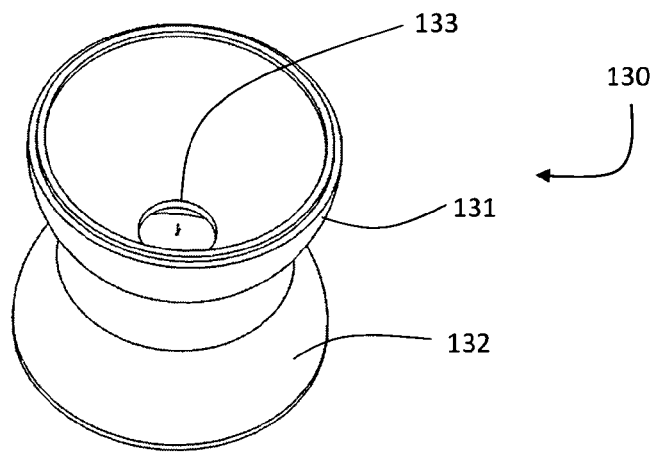
FIG. 14 shows a mid-section repeat unit.
Figure 15:
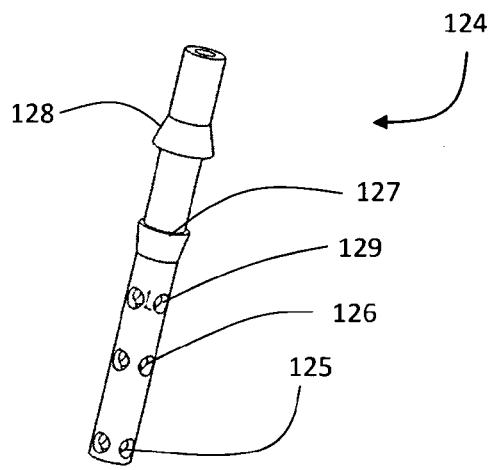
FIG. 15 shows a plunger and FIG. 16 shows an end cap.
Figure 16:
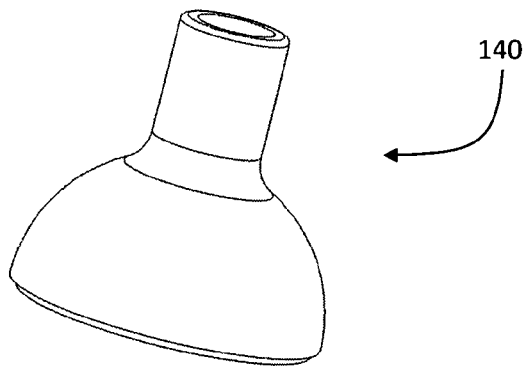
Figure 18:
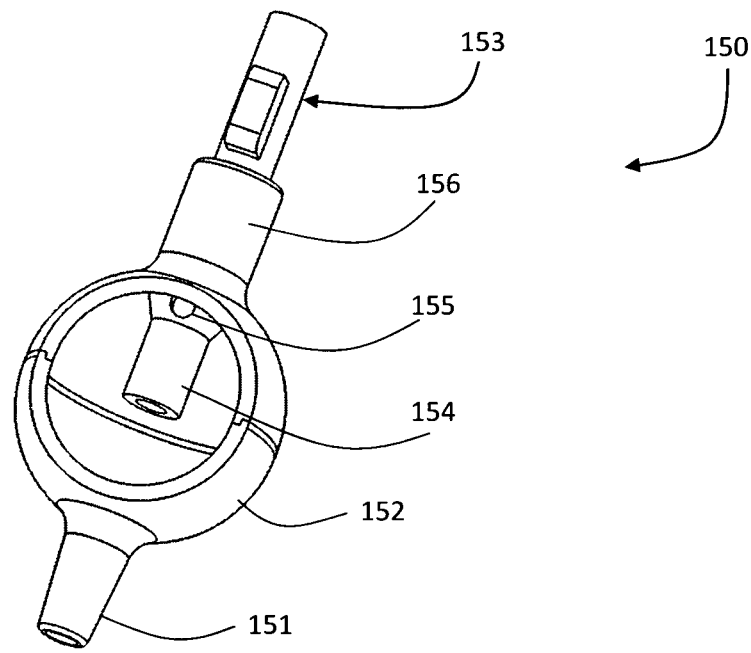
FIG. 18 is a similar view showing a use mode.
Figure 17:
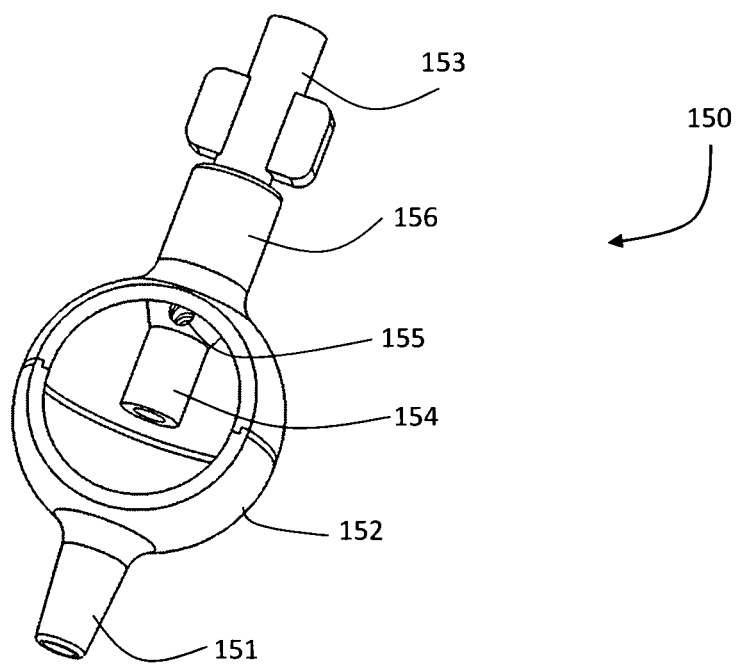
FIG. 17 is a partly cut away perspective view of an entrapment device having a twist-operation valve for switching between venting and use modes, showing a venting mode.
Figure 19:
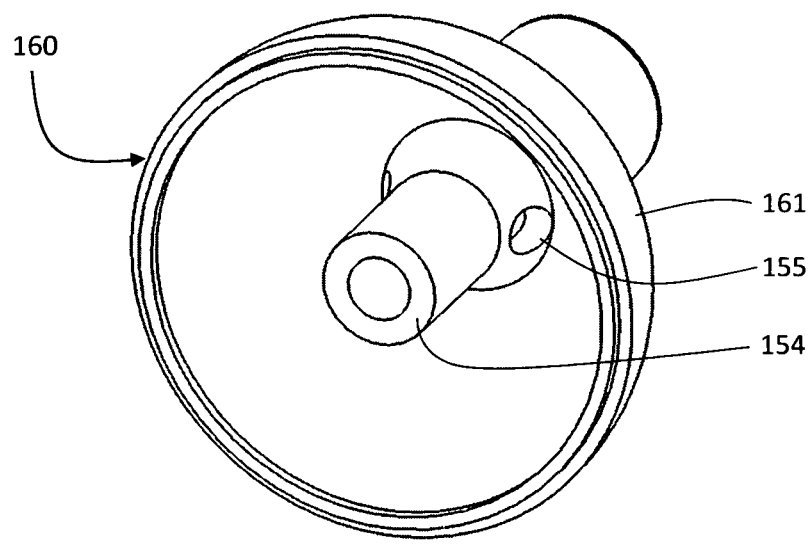
FIG. 19 shows an outlet cap.
Figure 20:
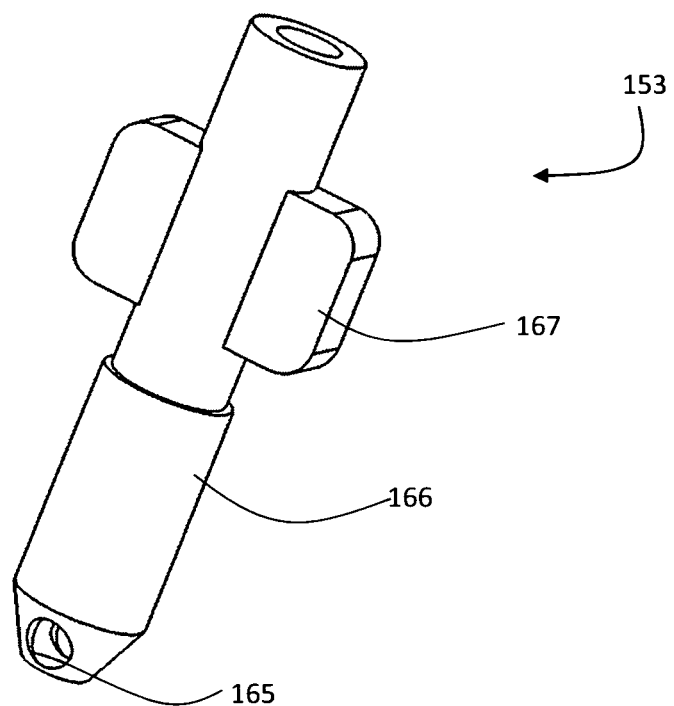
FIG. 20 shows the twist valve.
Figures 21A, 21B:
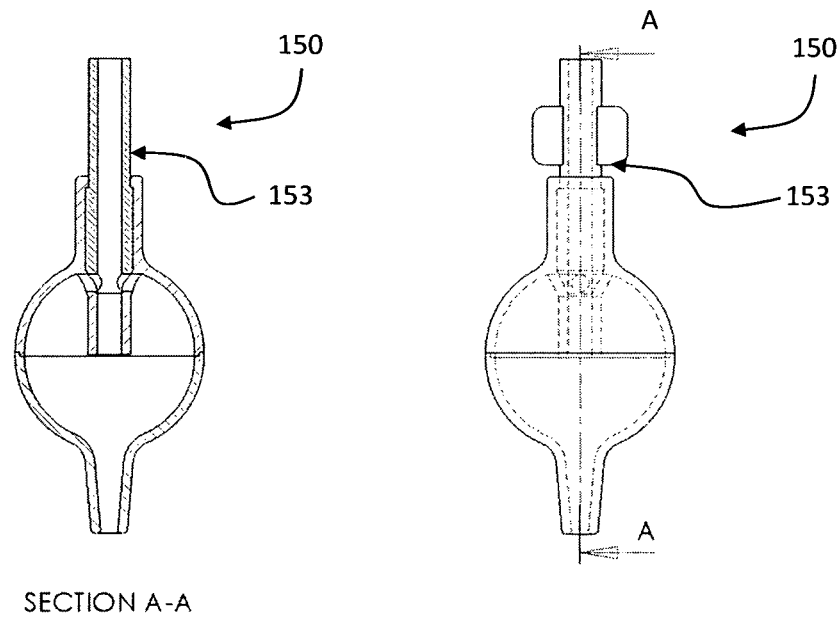
FIGS. 21(a) and 21(b) are side and cross-sectional views showing the vent position.
Figures 22A, 22B:
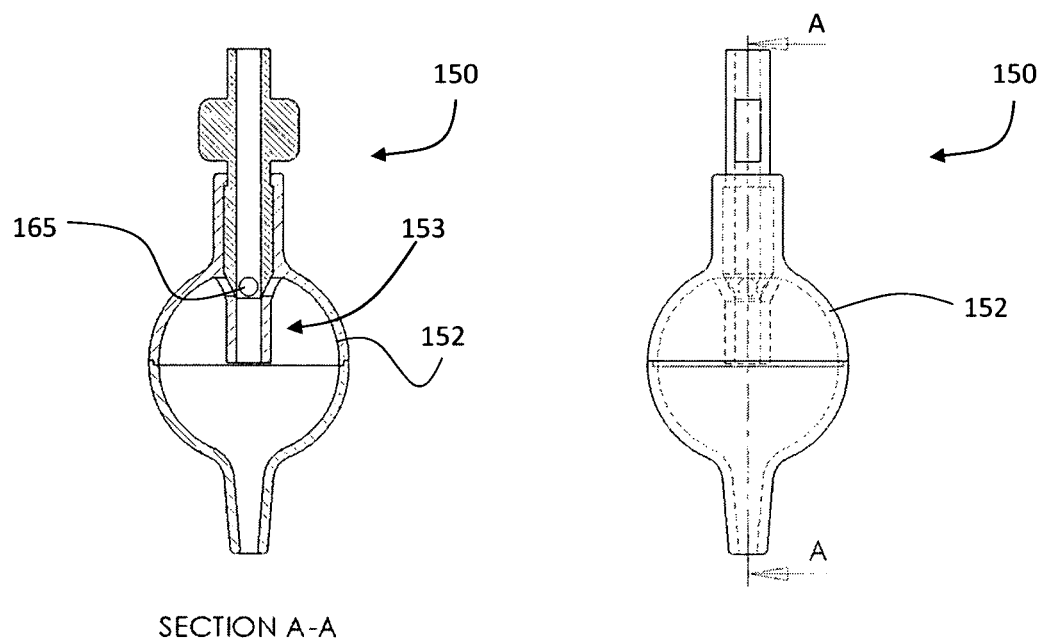
FIGS. 22(a) and 22(b) are similar views showing the use position.
Figures 23A, 23B:
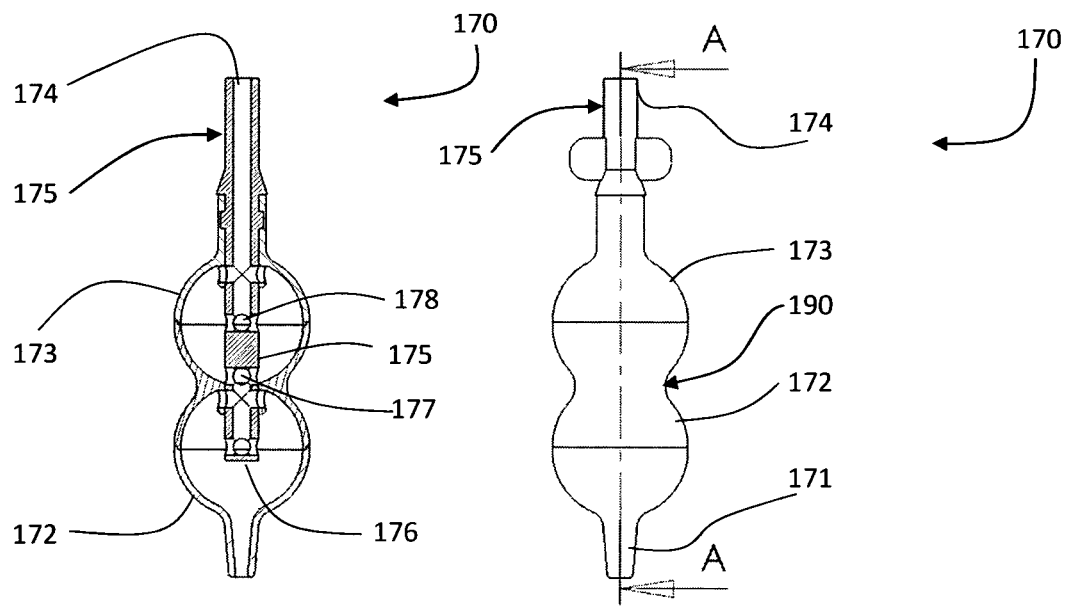
FIGS. 23(a) and 23(b) are side and cross-sectional views of a version of the device of FIGS. 17 to 22 having two chambers, and being in the venting mode.
Figures 24A, 24B:
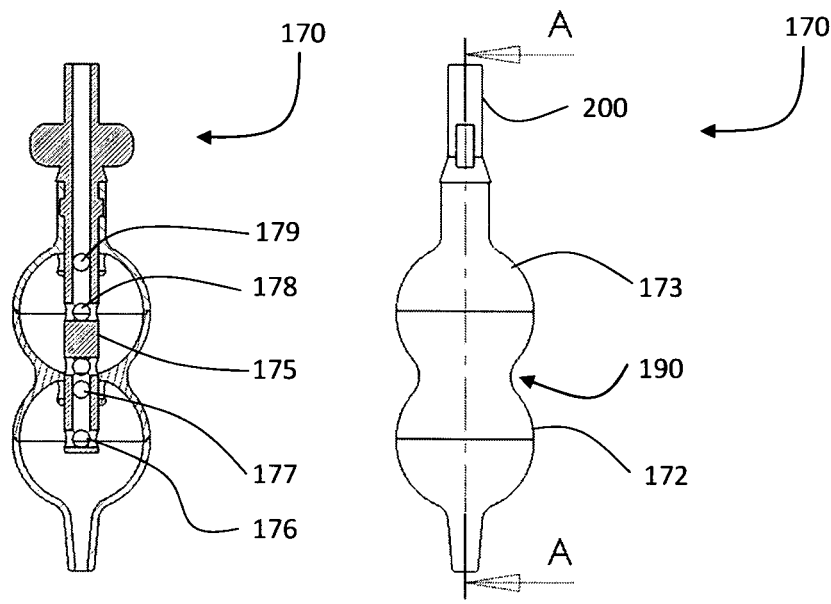
FIGS. 24(a) and 24(b) are similar views when in a use mode.
Figure 25:
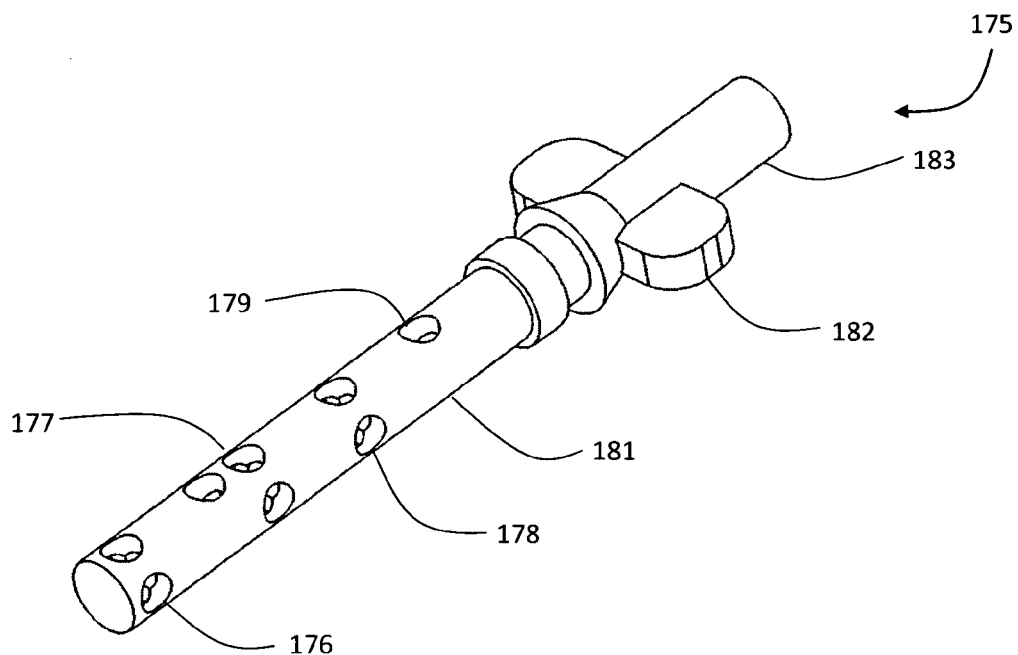
FIGS. 25 and 26 show a twist valve.
Figure 26:
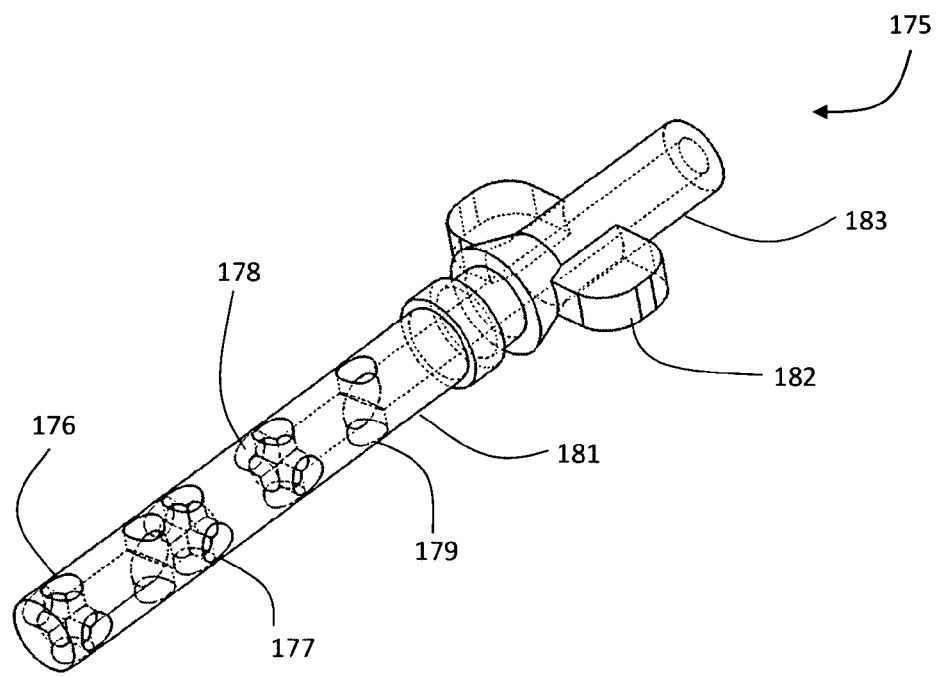
Figure 27:
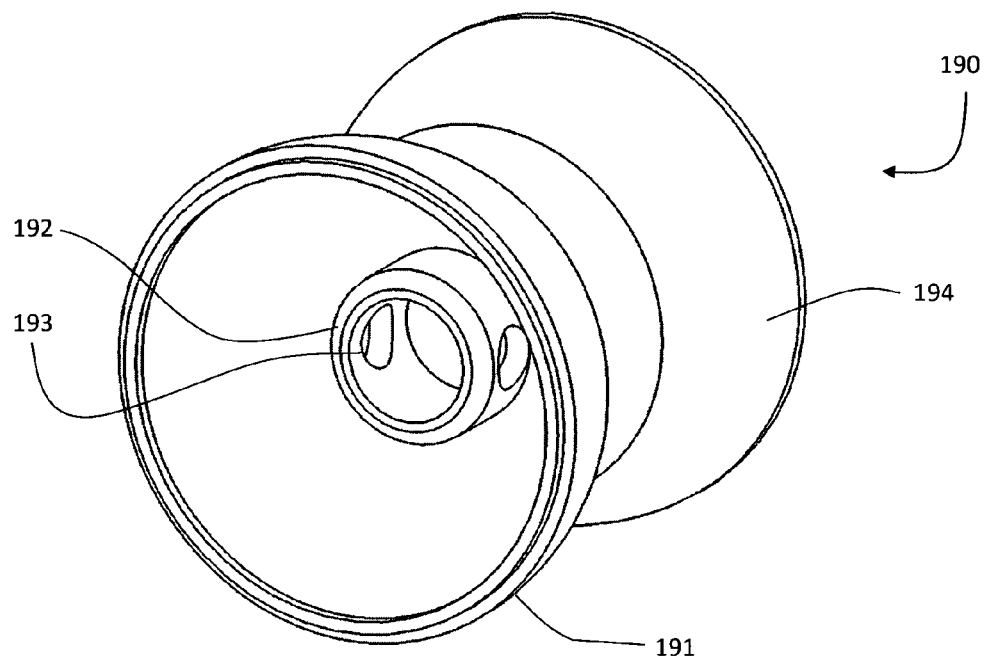
FIGS. 27 and 28 show a mid-section repeat unit.
Figure 28:
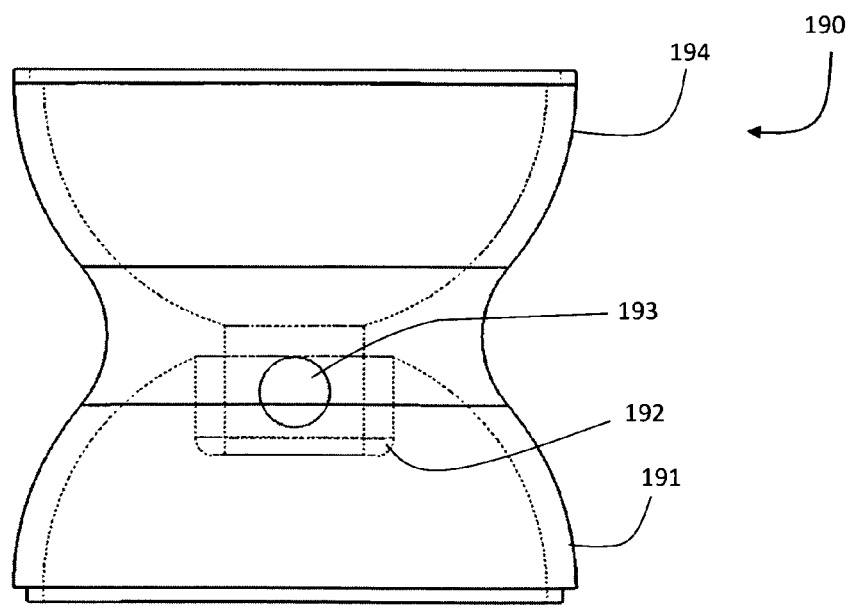
Figure 29:
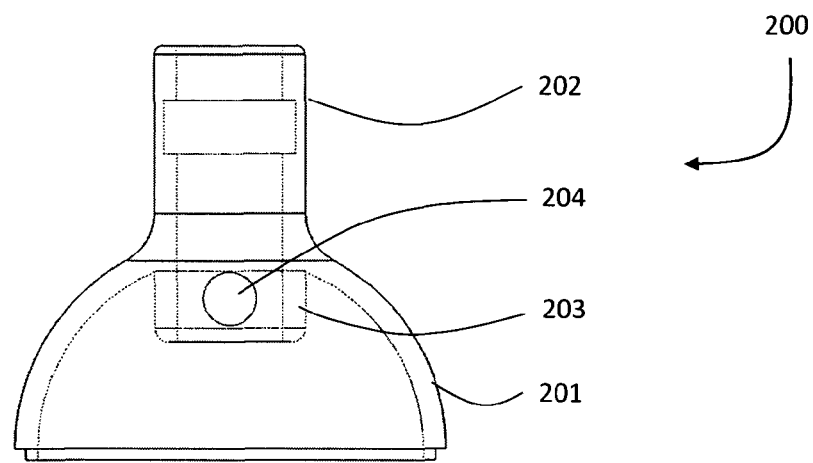
FIG. 29 shows an outlet cap.
Figure 30:
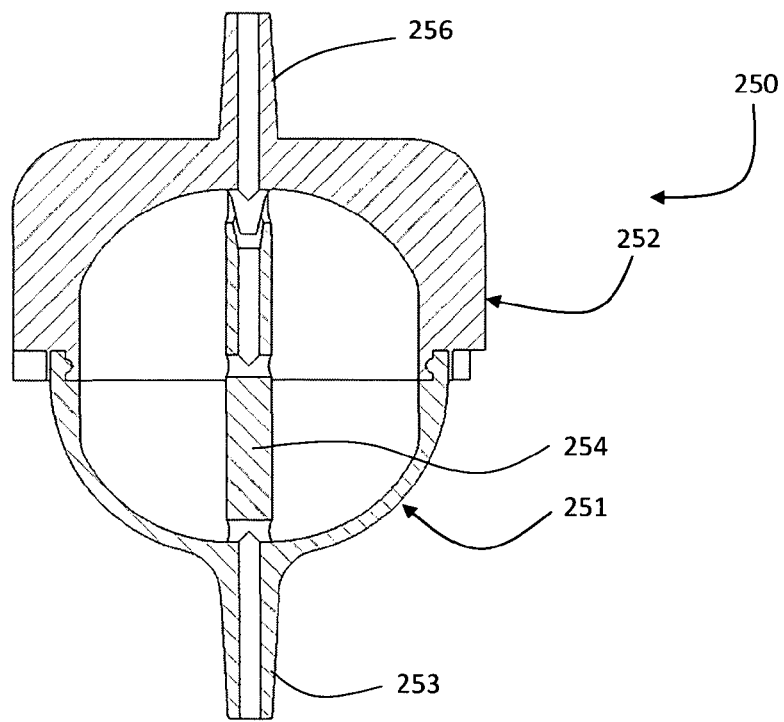
Figure 31:
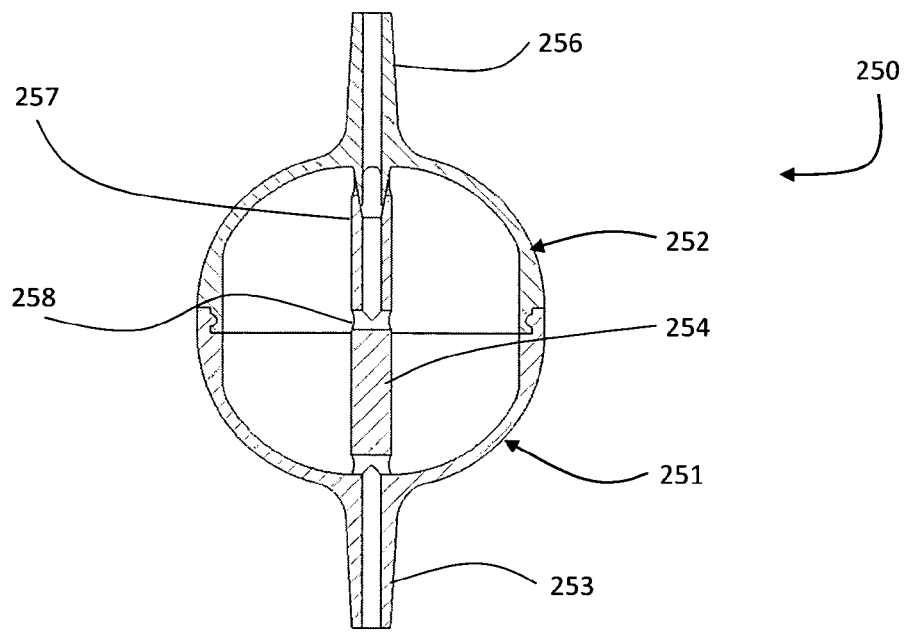
Figure 32:
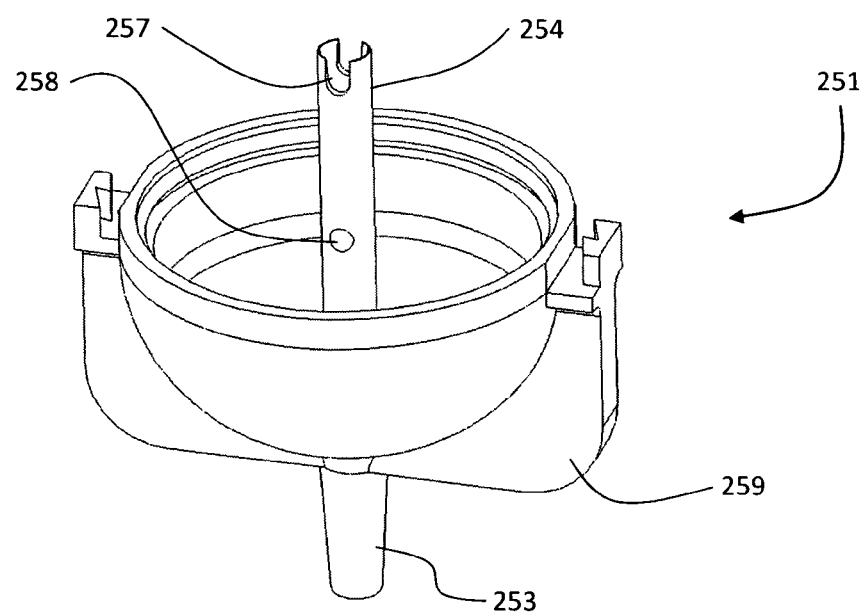
Figures 33, 34:
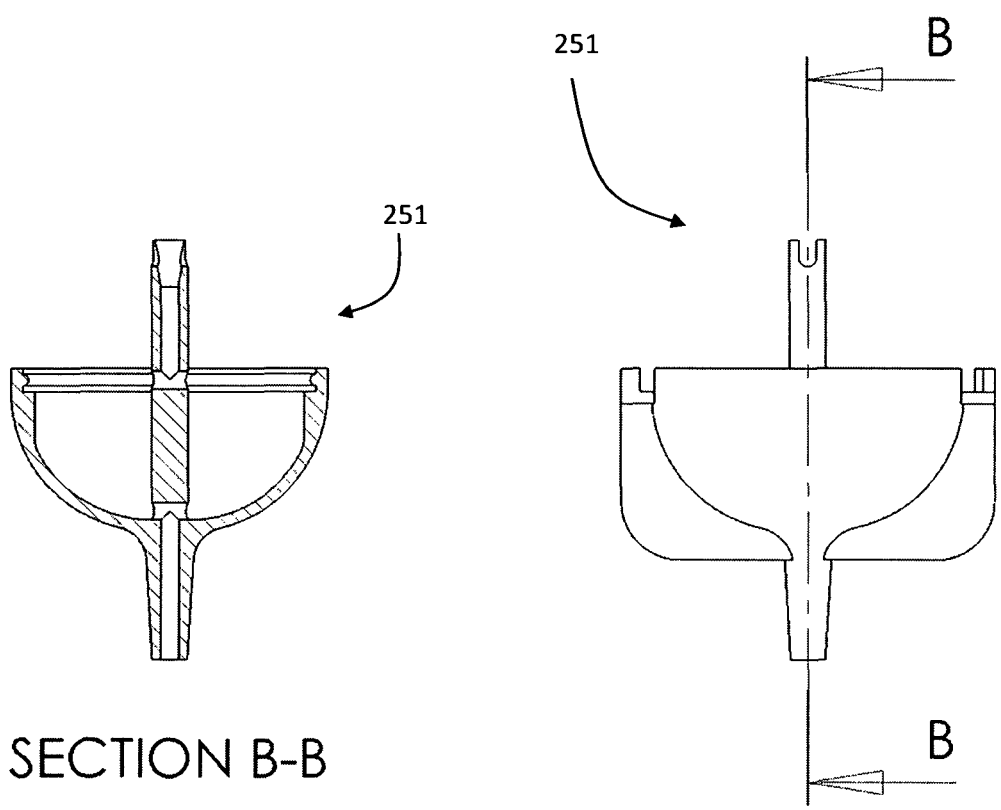
Figure 38:
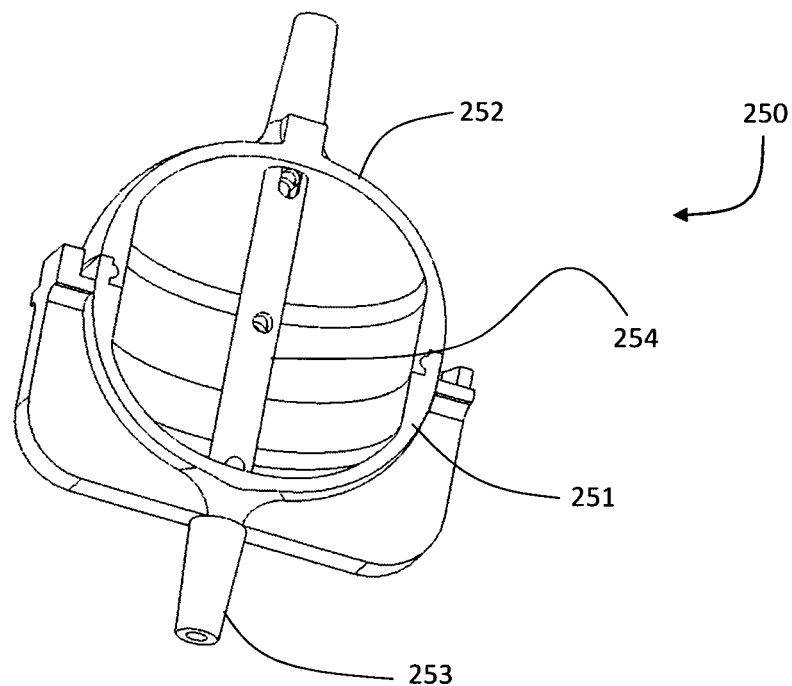
Figure 39:
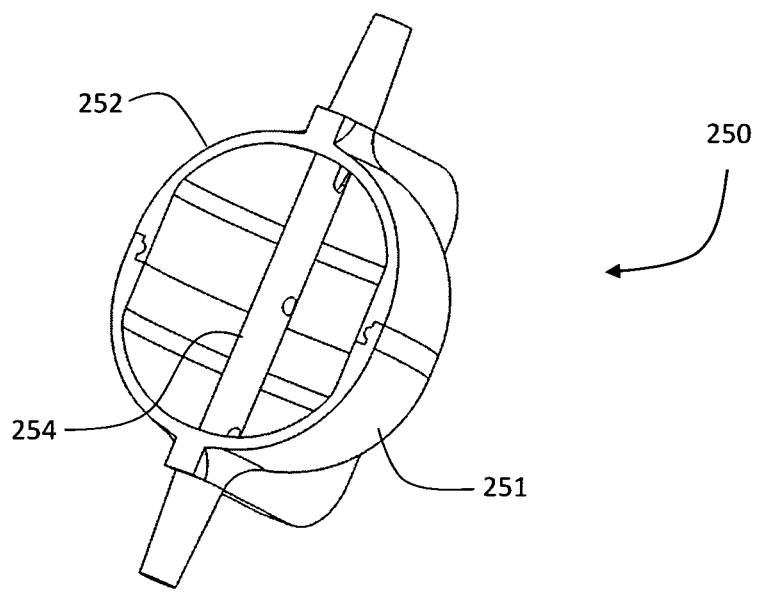

Referring to FIGS. 12 to 16 a device 120 has chambers 121 and 122, a device inlet 123, and a valve plunger 124. The plunger 124 has ports 125, 126 and 129, a catch 127 and a stop ridge 128. The venting mode is shown in FIG. 12, the ports 125 and 129 allowing bubble flow-through. The use mode is shown in FIG. 13, the ports 125 and 129 being chamber outlet ports centrally located in the chambers, and the port 126 links the chambers for liquid flow. FIG. 14 shows a mid-section modular unit 130 having a top cup 131, a bottom cup 132, and an opening 133 in-between. An outlet cap 140 for the device is shown in FIG. 16.

The valve for switching between the venting and in-use modes may be operable by a rotational or twisting action. Referring to FIGS. 17 to 22 a device 150 has a device inlet 151, a chamber 152, a conduit 154, a valve member 153, a chamber outlet port 155, and a sleeve 156 for the valve member 153. The valve member 153 has a lower port 165, a main tube 166, and handles 167. An outlet cap 160 has a cup 161, the conduit 154, and the chamber outlet port 155.

For venting, the chamber outlet port 155 and the valve port 165 are in registry. For use, they are not in registry, and flow is only through the conduit 154.

FIGS. 23 to 29 show a variant in which a device 170 has an inlet 171, a first chamber 172, a second chamber 173, a device outlet 174, and a valve 175. The latter has an elongate tube 181 with groups of ports 176, 177, 178, and 179 from bottom up (in orientation shown), handles 182, and an outlet tube 183. A mid-section modular unit 190 has a cup 191, a conduit 192, a chamber outlet port 193, and an upper cup 194. A device outlet cap 200 has a cup 201, an outlet tube 202, a valve part 203, and a chamber outlet 204. This device operates in the same manner as the above device (where the valve unit acts as a conduit), except having two chambers served by a single valve.

A device 250 shown in FIGS. 30 to 39 has venting/use valving without need for a separate valve member. It is made from only two parts, namely a bottom part 251 and a top part 252. There is an inlet 253, an integral valve member 254 on the bottom part 251, and an outlet 256 on the top part 252. The valve member 254 has end openings 257 and an opening 258 along its length. The top part 252 has a valve component 266 on the inside, and a handle 265 on the outside.

As shown, mutual rotation of the two parts 251 and 252 causes opening and closing of a valve so that the openings 257 are operative (venting) or the opening 258 are operative (in-use).

A device of any embodiment may be connected in an infusion line so that it forms part of an infusion system, or indeed of any medical or veterinary system which supplies liquid to a human or animal body. When administering any liquid intravenously, there is a risk of air or gas being transferred to the blood stream. An accumulation of this will cause an air embolism with the potential for severe morbidity and mortality. To reduce this risk, the bubble trap can be used on the line of the intravenous catheter (i.e. an infusion giving set) to trap any air bubbles that may be in the fluid before they enter the patient. Examples of administering fluid intravenously are:

Radiocontrast injection for computerized tomography.
Intravenous therapy. This may be used to correct electrolyte imbalances, to deliver medications, for blood transfusion or as fluid replacement to correct, for example, dehydration.
Intravenous administration of anesthetics It will be appreciated that the invention provides for entrapment of bubbles in a very simple and effective manner. There is no need for manufacture of filters, and well-known plastics manufacturing techniques may be employed to manufacture the devices at a very low cost in high volumes. Another major advantage is that the devices operate at any orientation, the only requirement in the field being that the device inlet and outlet be correctly connected as the device is uni-directional. This is advantageous in many applications such as infusion systems as is it desired to vent the system initially. If, however, bubble entrapment is desired for both flow directions then the device may have multiple chambers at least one of which is facing in the opposite direction.

Figure 40:
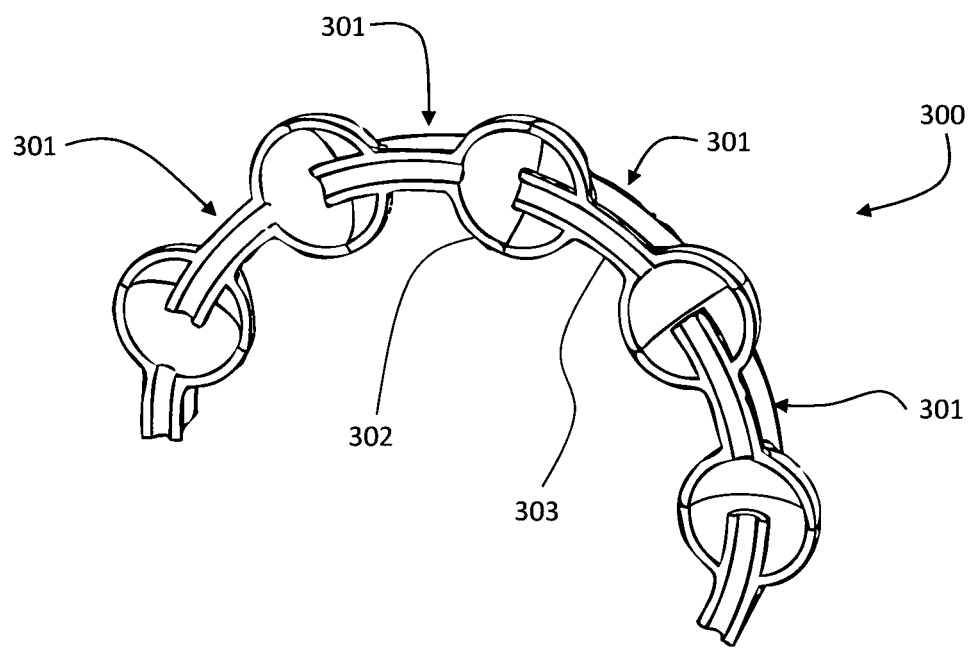
FIG. 40 is a perspective cut-away view of an alternative bubble entrapment device of the invention, for use as part of an infusion system, the device being suitable to be worn as a bracelet by a patient.

The invention is not limited to the embodiments described but may be varied in construction and detail. Successive chambers may be linked by a longer tube than illustrated in most embodiments. Where this is the case the device may be bent around, even to be fully bent around on itself to form a bracelet which can be worn by a patient. Such an arrangement in shown in FIG. 40, in which a device 300 has modular units 301 each having opposed parts forming chambers 302 with conduits, and an interconnecting tube 303. The end tubes of the device have fixtures, not shown, for interconnection to close the bracelet.

Also, manufacture may be on the basis of manufacturing two parts each being on one side of a plane through a device axis, each part extending along the full length of the device. Also, the device may be of a different material, such as a silicone-based plastics material or a polyethylene. It is preferably transparent or has a viewing window to allow visibility of the fluid. Also, a device of the invention may be adapted for use in other applications such as fuel lines.

In another alternative embodiment, the device may include a filter to block particles such as debris from a part of a vessel seal, or un-dissolved drugs. Such a filter may be in one or more chambers of the device. The pore size may be in the range of 5 µm to 20 µm.

The invention claimed is:

1. A bubble entrapment device comprising:
a device inlet for receiving a flow of liquid,
a device outlet for outlet of liquid flow, and
a chamber between said device inlet and said device outlet, the chamber including a volume,
wherein the chamber has an inlet port and an outlet port for liquid flow through the chamber, and
wherein the chamber outlet port is located on a conduit and is within the chamber volume, providing in use a space for total entrapment of bubbles within the chamber above the chamber outlet port, wherein the conduit and the chamber collectively establish the innermost space in the device.

2. The bubble entrapment device of claim 1, wherein the chamber is fluid tight between the inlet port and the outlet port.

3. The bubble entrapment device of claim 1, wherein the chamber is non-porous between the inlet port and the outlet port.

4. The bubble entrapment device of claim 1, wherein the chamber is completely fluidically sealed between the inlet port and the outlet port.

5. The bubble entrapment device of claim 1, wherein the chamber establishes a volume bounded by an interior surface area having only two openings through which fluid can pass, the first opening being the inlet port and the second opening being the outlet port.

6. The bubble entrapment device as claimed in claim 1, wherein the chamber has a chamber wall that solidly extends over a first hemisphere and over a second hemisphere opposite the first hemisphere, wherein the device is configured such that liquid flowing through the chamber comes into direct contact with the chamber wall.

7. The bubble entrapment device of claim 1, wherein the chamber includes surfaces that are inside the chamber, wherein the surfaces collectively establish a fluid tight surface assembly extending completely from the inlet port to the outlet port.

8. The bubble entrapment device of claim 1, wherein the chamber includes surfaces that are inside the chamber, wherein the surfaces collectively establish a gas tight surface assembly extending completely from the inlet port to the outlet port.

9. The bubble entrapment device of claim 1, wherein gas cannot escape from the chamber except through the inlet port and the outlet port.

10. A bubble entrapment device as claimed in claim 1, wherein there is a series of a plurality of chambers between the device inlet and the device outlet.

11. A bubble entrapment device as claimed in claim 1, wherein the chamber conduit has a funnel-shaped configuration.

12. A bubble entrapment device as claimed in claim 1, wherein there are a plurality of chambers and at least one chamber is linked by a tube with a next chamber.

13. A bubble entrapment device as claimed in claim 1, wherein the chamber external walls are substantially spherical in configuration.

14. A bubble entrapment device as claimed in claim 1, wherein the chamber is flexible to allow gas to be manually expelled by squeezing the chamber.

15. A bubble entrapment device as claimed in claim 1, wherein the chamber is of a transparent material.

16. A bubble entrapment device as claimed in claim 1, wherein the chamber is of a flexible material.

17. A bubble entrapment device as claimed in claim 1, wherein the device further comprises a filter to block unwanted particles.

18. A bubble entrapment device as claimed in claim 1, wherein the chamber outlet port is offset from a device central axis.

19. A bubble entrapment device as claimed in claim 18, wherein there are a plurality of chambers, and outlet ports of at least two chambers offset from the device axis.

20. A bubble entrapment device as claimed in claim 1, wherein the device is configured to be worn by a patient.

21. A bubble entrapment device as claimed in claim 20, wherein the device comprises connectors at ends so that it can form a loop such as a bracelet.

22. A bubble entrapment device as claimed in claim 1, wherein the device comprises a plurality of interconnected modular units.

23. A bubble entrapment device as claimed in claim 22, wherein the units comprise midsection units and end cap units, and at least one mid-section unit comprises a central tube and a cup configured to form portion of a chamber at each end.

24. A bubble entrapment device as claimed in claim 23, wherein said cup portions have an approximate hemispherical or cylindrical configuration.

25. A bubble entrapment device as claimed in claim 1, wherein the device further comprises a valve to switch the device between a venting mode at which bubbles are allowed to flow through the device and a use mode for bubble entrapment.

26. A bubble entrapment device as claimed in claim 25, wherein the valve comprises a lock to prevent switching back to a venting mode after it has been in the use mode.

27. A bubble entrapment device as claimed in claim 26, wherein the valve comprises a plunger comprising at least one chamber outlet port and forming a chamber conduit, the plunger being adapted to move longitudinally with respect to the chamber to move the chamber outlet port, and wherein the lock comprises a catch arranged to prevent sliding of the plunger from a use position to a venting position.

28. A bubble entrapment device as claimed in claim 25, wherein the valve is adapted to move a chamber outlet port from a location adjacent a chamber wall for the venting mode to a location within the chamber volume for the use mode.

29. A bubble entrapment device as claimed in claim 28, wherein the valve comprises a plunger comprising at least one chamber outlet port and forming a chamber conduit, the plunger being adapted to move longitudinally with respect to the chamber to move the chamber outlet port.

30. A bubble entrapment device as claimed in claim 29, wherein the device comprises a plurality of chambers, and the plunger extends into a plurality of chambers and has an outlet port for each of said chambers.

31. A bubble entrapment device as claimed in claim 25, wherein the valve comprises a rotatable member with at least one chamber outlet port, in which the chamber outlet port moves upon rotation of the valve member.

32. A bubble entrapment device as claimed in claim 31, wherein the valve has a handle for user gripping.

33. A bubble entrapment device as claimed in claim 31, wherein the valve comprises a fixed conduit and an inner or outer rotatable sleeve, the conduit and the sleeve having outlet ports, the valve having the venting mode when the ports are in registry.

34. A bubble entrapment device as claimed in claim 25, wherein the valve is integral with two chamber parts.

35. A bubble entrapment device as claimed in claim 34, wherein said two parts are mutually rotatable about a device axis, and each chamber part comprises an on-axis valve part, and said on-axis valve parts are configured to allow venting at one mutual position and to provide entrapment at another mutual position.

36. A bubble entrapment device as claimed in claim 35, wherein one valve part comprises a tube with at least one aperture at an end thereof, and the other valve part comprises a cover arranged to cover said aperture or apertures at one position for entrapment, and to leave them open at another position for venting.

37. A medical system comprising a tube for delivering a liquid to the body, the system comprising a bubble entrapment device according to claim 1 having its device inlet connected to a tube supply side and its device outlet connected to a tube delivery side.

38. A medical system as claimed in claim 37, wherein the system is an infusion system.

39. A bubble entrapment device comprising:
a device inlet for receiving a flow of liquid,
a device outlet for outlet of liquid flow, and
a chamber between said device inlet and said device outlet, the chamber including a volume,
wherein the chamber has an inlet port and an outlet port for liquid flow through the chamber, wherein the chamber has a first chamber wall that solidly extends away from the outlet port to a location adjacent a second chamber wall to which the first chamber wall is coupled, and
wherein the chamber outlet port is located on a conduit and is within the chamber volume, wherein the bubble entrapment device is configured to completely entrap bubbles in use in a space for entrapment of bubbles within the chamber above the chamber outlet port.

40. The bubble entrapment device of claim 39, wherein the chamber is fluid tight between the inlet port and the outlet port.

41. The bubble entrapment device of claim 39, wherein the chamber is non-porous between the inlet port and the outlet port.

42. The bubble entrapment device of claim 39, wherein the chamber establishes a volume bounded by an interior surface area having only two openings through which fluid can pass, the first opening being the inlet port and the second opening being the outlet port.

43. The bubble entrapment device as claimed in claim 39, wherein the chamber has a chamber wall that solidly extends over about a first hemisphere and over about a second hemisphere opposite the first hemisphere, wherein the device is configured such that liquid flowing through the chamber comes into direct contact with the chamber wall.

44. The bubble entrapment device as claimed in claim 39, wherein the chamber has a chamber wall that solidly extends over a first hemisphere and over a second hemisphere opposite the first hemisphere, wherein the device is configured such that liquid flowing through the chamber comes into direct contact with the chamber wall.

45. The bubble entrapment device of claim 39, wherein the bubble entrapment device is fluid tight between the inlet port and the outlet port.

46. The bubble entrapment device of claim 39, wherein interior surfaces of the chamber extend from the inlet port to the outlet port, the interior surfaces being non-porous between the inlet port and the outlet port.

47. The bubble entrapment device of claim 39, wherein innermost surfaces of the chamber extend from the inlet port to the outlet port and form a fluid tight barrier between the inlet port and the outlet port.

48. The bubble entrapment device of claim 39, wherein the chamber establishes an innermost container of the bubble entrapment device that is completely fluidically sealed between the inlet port and the outlet port.

49. The bubble entrapment device of claim 39, wherein the bubble entrapment device is configured to maintain the entrapped bubbles in direct contact with the liquid flowing through the chamber.

50. The bubble entrapment device of claim 39, wherein the device includes a single chamber.

51. The bubble entrapment device of claim 39, wherein the chamber is the innermost chamber of the bubble entrapment device.

52. The bubble entrapment device of claim 39, wherein the chamber is non-permeable to fluids between the inlet port and the outlet port.

53. The bubble entrapment device of claim 39, wherein the bubble entrapment device is hermetically sealed between the inlet port and the outlet port.

54. The bubble entrapment device of claim 39, wherein the chamber is completely fluidically sealed between the inlet port and the outlet port.

55. The bubble entrapment device of claim 54, wherein the chamber is completely established by two monolithic components.

56. The bubble entrapment device of claim 39, wherein the chamber includes surfaces that are inside the chamber, wherein the surfaces collectively establish a gas tight surface assembly extending completely from the inlet port to the outlet port.

57. The bubble entrapment device of claim 56, wherein the bubble entrapment device includes a channel that extends from a first location located within a space encompassed by the chamber to a second location located outside the space encompassed by the chamber, wherein the second location is located within the channel between a first end of the channel and a second end of the channel, wherein the first end of the channel is located within the space encompassed by the chamber.

58. The bubble entrapment device of claim 39, wherein:
wherein the bubble entrapment device is configured to entrap bubbles in use in the space for entrapment of bubbles such that gas of the bubbles cannot leave the chamber.

59. The bubble entrapment device of claim 58, wherein:
the first chamber wall, the second chamber wall and the conduit wall are the innermost structures of the device.

60. The bubble entrapment device of claim 39, wherein the chamber includes surfaces that are inside the chamber, wherein the surfaces collectively establish a fluid tight surface assembly extending completely from the inlet port to the outlet port.

61. The bubble entrapment device of claim 60, wherein the established fluid tight surface assembly has only two openings therein.

62. The bubble entrapment device of claim 60, wherein the surfaces are established by an assembly consisting of two monolithic components.

63. The bubble entrapment device of claim 60, wherein the chamber is non-permeable to fluids between the inlet port and the outlet port.

64. The bubble entrapment device of claim 60, wherein the established fluid tight surface assembly is a gas tight surface assembly which has only two openings therein.

65. A bubble entrapment device comprising:
a device inlet for receiving a flow of liquid,
a device outlet for outlet of liquid flow, and
a chamber between said device inlet and said device outlet, the chamber including a volume,
wherein the chamber has an inlet port and an outlet port for liquid flow through the chamber,
wherein the chamber outlet port is located on a conduit and is within the chamber volume such that the bubble entrapment device is configured to completely entrap bubbles within the chamber above the chamber outlet port while maintaining the entrapped bubbles in direct contact with the fluid flowing through the chamber.

66. The bubble entrapment device of claim 65 wherein the bubble entrapment device is fluid tight between the inlet port and the outlet port.

67. The bubble entrapment device of claim 65, wherein the bubble entrapment device is configured such that there are only two openings in the chamber, the two openings being the inlet port and the outlet port.

68. The bubble entrapment device of claim 65, wherein the chamber is established by an assembly consisting of two monolithic components.

69. The bubble entrapment device of claim 65, wherein:
wherein the chamber establishes the innermost space surrounding the conduit, and the device is configured to prevent gas from leaving the innermost space other than through the inlet and the outlet.

70. The bubble entrapment device of claim 65, wherein:
wherein the bubble entrapment device is configured to entrap bubbles such that the bubbles remain trapped and do not leave the chamber.

71. A bubble entrapment device comprising:
a device inlet for receiving a flow of liquid,
a device outlet for outlet of liquid flow, and
a chamber between said device inlet and said device outlet,
wherein the chamber has an inlet port and an outlet port for liquid flow through the chamber, and
wherein the chamber outlet port is located on a conduit and is within the chamber volume, providing in use a space for entrapment of bubbles within the chamber above the chamber outlet port, wherein the chamber has a chamber wall that solidly extends over about a first hemisphere and over about a second hemisphere opposite the first hemisphere, wherein the device is configured such that liquid flowing through the chamber comes into direct contact with the chamber wall.

* * * * *